United States Patent [19]

Sommer et al.

[11] Patent Number: 4,934,183
[45] Date of Patent: Jun. 19, 1990

[54] EXCESS AIR CONTAMINATION LEVEL INDICATOR

[75] Inventors: Holger T. Sommer, Greenbelt; Charles F. Harrison, Adelphi, both of Md.

[73] Assignee: Pacific Scientific Company, Newport Beach, Calif.

[21] Appl. No.: 358,637

[22] Filed: May 30, 1989

[51] Int. Cl.⁵ ............................................. G01N 15/00
[52] U.S. Cl. ................................... 73/118.1; 356/438
[58] Field of Search ............... 73/118.1; 356/438, 437, 356/439; 364/555; 377/11; 340/627; 250/574

[56] References Cited

U.S. PATENT DOCUMENTS

| | | | |
|---|---|---|---|
| 4,302,754 | 11/1981 | Magee et al. | 340/631 |
| 4,441,513 | 4/1984 | Herwig | 356/436 X |
| 4,491,926 | 1/1985 | Okada et al. | 364/555 |
| 4,677,426 | 6/1987 | Dattilo | 340/627 |

Primary Examiner—Jerry W. Myracle
Attorney, Agent, or Firm—Lane & Aitken

[57] ABSTRACT

In an air contamination level detector for detecting the degree of contamination of the intake air to an internal combustion engine, a laser beam is directed through the intake air stream and light scattered from particles in the intake air stream are detected by a photodetector to generate a pulse for each particle. Pulses over a given size are used to enable an AND gate to pass high frequency pulses to a counter, which is periodically recycled. The count accumulated in the counter represents the duty cycle of the pulses and the dirtiness of the intake air. When the count in the counter reaches a preselected level, it causes a warning light to be energized to indicate that the intake air has a exceeded a tolerance level.

6 Claims, 2 Drawing Sheets

EXCESS AIR CONTAMINATION LEVEL INDICATOR

This invention relates to an air contamination concentration detector and more particularly to such a detector designed to signal a warning when the contamination level of the intake air of an air breathing engine exceeds a predetermined level of tolerance.

BACKGROUND OF THE INVENTION

A need exists for a relatively inexpensive device which will indicate when the contamination in the intake air of an air breathing engine, such as an internal combustion engine, becomes excessive. However, since the contamination consists of a distribution of particle sizes of various materials and shapes, precisely defining a single parameter which will correlate with the harmfulness of the contamination in the intake air presents difficulties. One parameter which correlates fairly well with the degree of engine wear caused by the contamination and, accordingly, with the tolerability of the contamination level is the number of particles above a selected minimum size per unit volume in the intake air. Technology exists for counting particles in an air stream. In such systems, the air stream is passed through a light beam and the light scattered from particles in the air stream are detected by photodetectors to generate pulses, which can be counted to provide an indication of the number of particles per unit time. However, the sensors in this technology respond to particles of different sizes, shapes, and materials in different ways. In addition, variations in the location of a particle passing through the light beam causes a variation in the response. As a result, a full analysis of the response of such sensors is quite complex. Moreover, the intake air of an internal combustion engine has a widely varying velocity so that a count of pulses per unit of time will not provide an indication of the number of particles per unit volume in the intake air under normal operating conditions.

SUMMARY OF THE INVENTION

The pulses generated by the photodetector in particle sensors depend mainly on the particle size and the brightness of the beam. The system of the present invention generates a laser beam, the brightness of which varies across a portion of the active volume of the intake air and there is a hot spot produced inside of an air intake conduit at a focus point with the intensity decreasing with displacement from this focus point. A small particle passing through the hot spot will generate as much signal as a larger particle passing through the side of the beam. Only pulses of a predetermined amplitude are counted to discriminate against smaller particles. The effect of nonuniform beam illumination makes the unit more efficient in detecting large particles than small ones. This is precisely the behavior desired in evaluating the functional contamination level; that is, the degree with which the contamination level causes engine wear.

To account for the variation in the intake air velocity, instead of counting the number of pulses per unit time, the duty cycle of the pulse train generated by the photodetector is measured and when the duty cycle of the pulse train exceeds a predetermined value, a warning signal is generated.

The duty cycle of the particles large enough to generate pulses over the threshold level provides a good indication of the functional contamination level because at higher flow rates, a greater number of pulses per unit time will be generated, but the pulses will be of shorter duration because the residence time of the particles in the light beam will be less. Assuming a fixed level of air contamination, a high flow rate will lead to more shorter pulses whereas a lower flow rate will have fewer longer pulses, but the duty cycle of the pulses over a given time interval should be the same for both flow rates.

In accordance with the present invention, a circuit is provided to indicate when the duty cycle of the pulse train generated by the photodetector exceeds a predetermined level by using the pulse train generated by the photodetector to gate a high frequency oscillator into a counter and resetting the counter to zero at predetermined counts. When the counter counts up to a predetermined level, this will indicate that the duty cycle has exceeded the threshold and this occurrence causes a warning signal to be generated. In this manner, a relatively inexpensive but accurate indicator is provided which will give a warning when the functional level of the contamination exceeds a permissible level of tolerance.

DESCRIPTION OF THE PREFERRED EMBODIMENT

Figure 1:
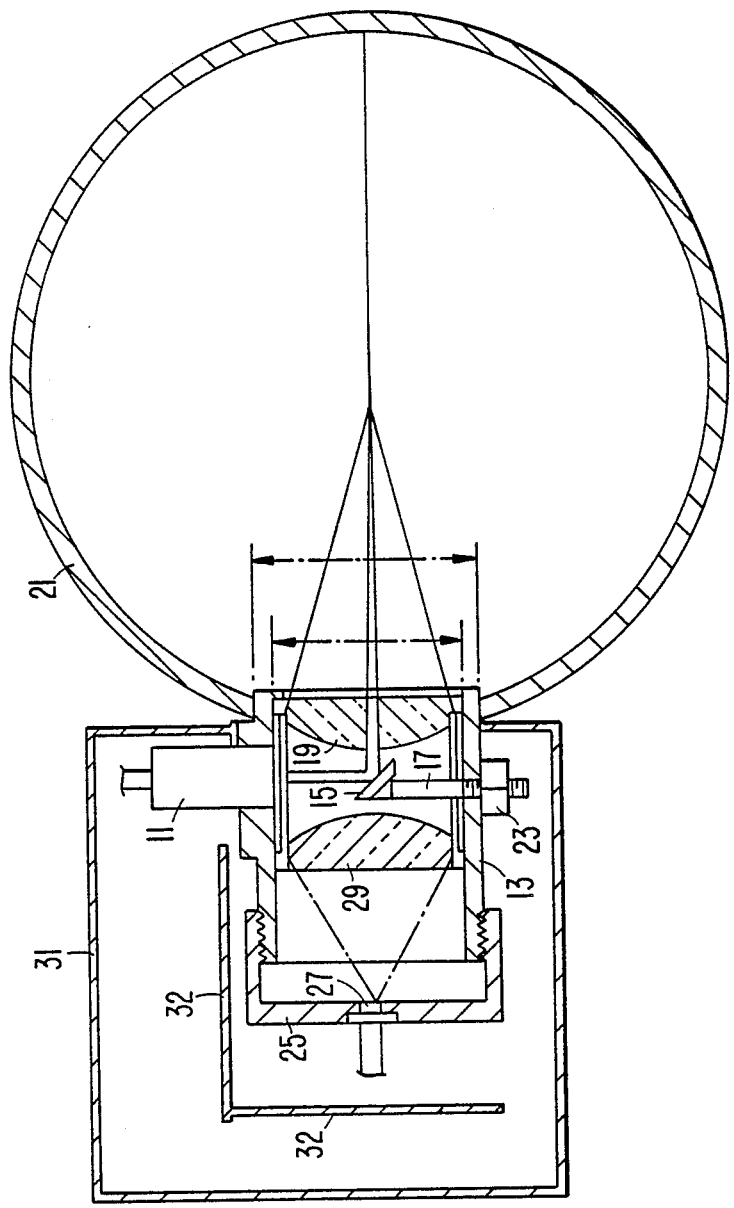
FIG. 1 illustrates the particle detecting cell employed in the instrument of the present invention.

As shown in FIG. 1, the detector of the present invention comprises a laser diode 11 with collimating optics mounted on a tubular lens holding frame 13 into which the laser beam generated by the laser diode 11 is directed. A mirror 15 is mounted on a post 17 in the center of the lens holder 13 to receive the laser beam and reflect it through a lens 19, which is mounted in the lens holder 13. The laser beam upon passing through the lens 19 enters a conduit 21 through which the intake air of the air breathing engine is directed. The lens 19 focuses the laser beam to a narrow beam in the interior of the conduit 21 with an intensity distribution comprising a high intensity or hot spot at the center of the beam and falling off to lower intensities at the edges of the beam. The post 17 is provided with threads to engage corresponding female threads in a bore passing through the lens holder 13, so as to be able to adjust the position of the mirror 15 in the center of the lens holder 13. A nut 23 threaded onto the end of the post serves to lock the post in position once it has been properly adjusted. The back end of the lens holder 13 is provided with external threads to mate with internal threads on a cap-shaped mount 25 for mounting a photo diode 27 on the axis of the lens holder 13. By means of the threaded engagement between the mount 25 and the lens holder 13, the axial position of the photo diode 27 can be finely adjusted. A second lens 29 is axially mounted in the lens holder 13 on the opposite side of the mirror 15 from the lens 19. The lenses 19 and 29 operate to focus light scattered from the hot spot inside the conduit 21 onto the photo diode 27. The lens holder 13, the mount 25, and the laser diode 11 are all enclosed in a housing 31, which also encloses the electronics of the system mounted on circuit boards 32.

In operation, a particle encountering the laser beam hot spot will scatter light in all directions. The light backscattered from the hot spot will be collected by the lenses 19 and 29 and focused on the photo diode 27. As a result, each particle passing through the laser beam hot spot inside the conduit 21 will cause the photo diode 27 to generate a pulse.

Figure 2:
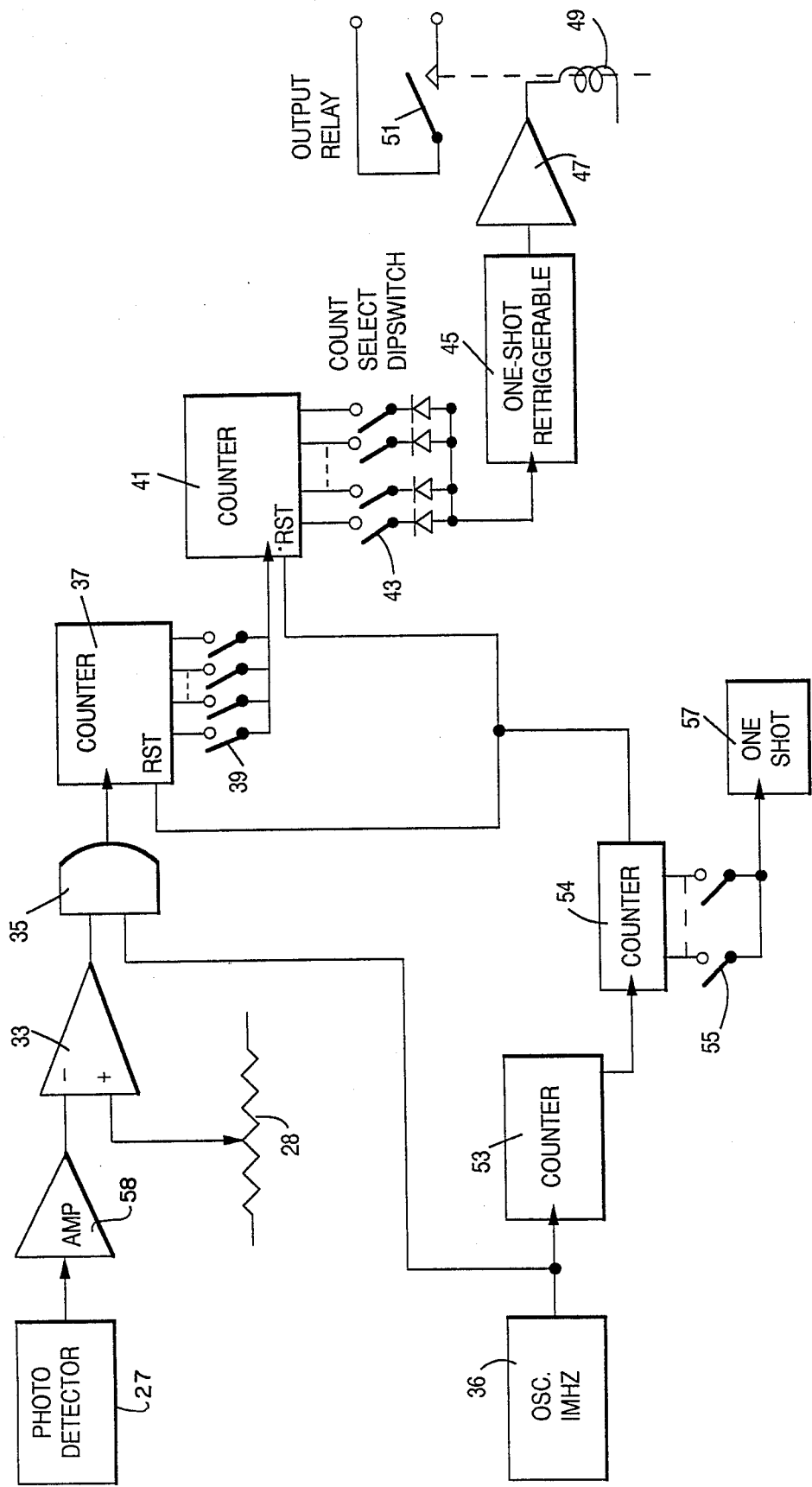
FIG. 2 is a block diagram of the circuitry employed in the system of the present invention.

Pulses generated by the photo diode 27 in response to particles are amplified by amplifier 58. The output of the amplifier 58 will be negative going pulses. As shown in FIG. 2, these negative going pulses are applied to the negative side of a differential comparator 33, the positive side of which is connected to the tap of potentiometer 28 operable to apply a threshold voltage to the differential comparator variable from 0 to minus one volt. As a result, the differential comparator 33 will subtract the threshold voltage from each of the applied pulses so that only pulses having an amplitude greater than the threshold voltage are passed through to an AND gate 35, which is also connected to receive one megahertz pulses from an oscillator 36. As a result, each negative going pulse having an amplitude greater than the threshold voltage, will enable the AND gate 35 and cause the AND gate 35 to pass the one megahertz pulses from the oscillator 36 for the duration of the applied pulse from the differential amplifier 33. Each pulse passing through the AND gate 35 is counted by a counter 37, the capacity of which is controlled by dip switches 39. Each time the counter 37 reaches its capacity and recycles to 0, it applies a pulse to a counter 41, which is connected via count select dip switches 43 to a one-shot retriggerable multivibrator 45. When the counter 41 reaches a count selected by dip switches 43, it applies an output pulse to the one-shot multivibrator 45 triggering the multivibrator 45 and causing it to generate a one second output pulse. The output pulse from the one shot multivibrator 45 is amplified by an amplifier 47 and applied to the coil 49 of a relay, which in response to receiving a pulse from an amplifier 47 will close a switch 51 to energize a warning light.

The one megahertz output from the oscillator 36 is counted by a counter 53, which recycles and produces an output pulse approximately once every 64 milliseconds. The output pulses produced by the counter 53 are counted by a counter 54, which is connected by count selecting dip switches 55 to a one-shot multivibrator 57. The dip switches 55 select the count at which the counter 54 recycles and applies a pulse to the one-shot multivibrator 57. By means of the dip switches, the counter 54 can be adjusted to recycle in a range from 128 milliseconds to 16 seconds. When the counter 54 produces an output pulse, it triggers the one shot multivibrator 57 which then generates a one-microsecond output pulse applied to the counters 37 and 41 to reset these counters. As a result, the circuit will trigger the one shot retriggerable multivibrator 45 to cause it to energize the warning light if the counter 41 receives enough pulses to overflow before being reset, in response to the counter 54 recycling.

With this arrangement, the relay 49 will be energized to turn on the warning light whenever the duty cycle of the output pulses of the differential comparator 33 rises above a preselected duty cycle value, which is selected by the dip switches 39, 43 and 55. Thus, the warning light will be energized when the duty cycle of output pulses of the photodetector 27, having an amplitude greater than the threshold voltage set by the potentiometer 28, is greater than the preselected duty cycle value. By responding to the duty cycle of the pulses caused by particles over a given magnitude, the system will energize the warning light when the number of particles per unit volume over a minimum size exceeds a predetermined value, regardless of the speed of the air passing through the inlet conduit 21. When the air intake has a relatively low velocity, as when the engine is idling, the particles will be in the laser beam longer and thus, cause the pulses generated by the photodetector 27 to be longer. Thus, in a given output pulse from the photodetector 27, a greater number of cycles from the oscillator 37 will be counted by the counter 37. On the other hand, when the air intake has a rapid velocity, the pulses produced by the photodetector 27 will be shorter, but a greater number of pulses will produced per unit time in the output pulse train from the photodetector. As a result, over a given unit of time, the count accumulated by the counters 37 and 41 will tend to be the same regardless of the speed of the intake air and will not depend upon the number of pulses per unit time passing through the laser beam, but instead, the count accumulated at the time of resetting by the output of the one shot multivibrator will vary with the duty cycle of pulses. This duty cycle, in turn, will vary with the number of the larger particles per unit volume and thus, will provide a good indication of the dirtiness of air passing through the intake conduit. In this manner, the operator is provided with a good indication of when the air being received by the engine is too dirty and requires corrective action. For example, the intake air may become dirty because the air filter has become torn or is badly seated. Alternatively, the intake air may become too dirty because of the environment in which the engine is operated and require more frequent air cleaner and oil changes than when operating under conditions when the air is less dirty.

The above description is of a preferred embodiment of the invention and many modifications may be made thereto without departing from the spirit and scope of the invention, which is defined in the appended claims.

We claim:

1. A system for determining when the dirtiness of an air stream exceeds a predetermined maximum comprising means to generate pulses in a pulse train in response to particles in said stream, each pulse being generated in response to a different particle in said stream and the duration of each pulse varying with the velocity of said stream, and means to sense the duty cycle of said pulses and to generate an output signal when the duty cycle of said pulses rises above a selected value.

2. A system as recited in claim 1, wherein said means to detect the duty cycle comprises a source of high frequency pulses, a counter connected to count said high frequency pulses when a pulse in said pulse train is present, means to periodically reset said counter, and means to generate said output signal when said counter reaches a preselected magnitude.

3. A system as recited in claim 1, wherein said gas stream is the air intake of an internal combustion engine.

4. A system as recited in claim 1, wherein said means to generate a pulse train comprises means to direct a light beam into said stream, photodetecting means to detect light scattered from said light beam to generate said pulses in response to said particles in said stream.

5. A system as recited in claim 4, wherein said means to direct a light beam into said stream comprises a mirror positioned to reflect said light beam into said stream, a lens positioned to focus the light beam reflected from said mirror towards the center of said stream, means including said lens to collect light scattered from said light beam by particles in said stream and to direct the scattered light onto said photodetecting means.

6. A system as recited in claim 1, wherein the amplitude of the pulses in said pulse train vary in accordance with the size of particles in said stream, and wherein said means to sense the duty cycle of said pulses and said pulse train responds only to pulses having amplitudes greater than a predetermined value.

* * * * *